(12) United States Patent
Josephk et al.

(10) Patent No.: US 7,732,558 B2
(45) Date of Patent: Jun. 8, 2010

(54) DENDRITIC COMPOUND AND USE THEREOF

(75) Inventors: Abraham Josephk, Hsinchu (TW); Hui-Ju Cho, Lugang Township, Changhua County (TW); Yu-Hau Shih, Sindian (TW); Chao-Hung Kao, Taipei (TW); Huang-Chien Liang, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 644 days.

(21) Appl. No.: 11/316,822

(22) Filed: Dec. 27, 2005

(65) Prior Publication Data

US 2006/0165601 A1    Jul. 27, 2006

(30) Foreign Application Priority Data

Dec. 30, 2004   (TW) .............................. 93141379 A

(51) Int. Cl.
    *C08G 69/44*    (2006.01)
    *A61B 5/055*    (2006.01)
(52) U.S. Cl. ................... 528/292; 560/155; 560/168; 560/169; 560/171; 424/1.11; 424/1.65; 424/9.1; 424/9.3; 424/9.32; 534/15
(58) Field of Classification Search ............... 534/15; 560/155, 168, 169, 171; 424/1.11, 1.65, 424/9.1, 9.3, 9.32; 528/292, 272
See application file for complete search history.

(56) References Cited

U.S. PATENT DOCUMENTS 5,958,372 A * 9/1999 Ladd ....................... 424/1.65
6,982,324 B1 * 1/2006 Lu et al. ................... 534/15

OTHER PUBLICATIONS

E.Gillies, J.Fretchet, "Designing Macromolecules for Therapeutic Applications" Published on Web Nov. 1, 2002.*

* cited by examiner

*Primary Examiner*—Milton I Cano
*Assistant Examiner*—Gennadiy Mesh
(74) *Attorney, Agent, or Firm*—Bacon & Thomas, PLLC

(57) ABSTRACT

A dendritic compound of the following structure: $PD_n$-Z-L is disclosed. In the structure above, P is X—$(CH_2CH_2$—O$)_r$—, r is an integer ranging from 1000 to 4000, X is OH, $NH_2$, or OR, R is $C_1$ to $C_{10}$ alkyl, $D_n$ is a residue of branched $C_3$ to $C_{30}$ polyol compounds, n is the quantity of layers of the residue of branched compounds and is an integer equal to or greater than 1, L is a metal cation, Z is the residue of a $C_3$ to $C_{30}$ compound with multi functional groups. The functional groups illustrated above can be carboxylic groups, amino groups, amide groups, or chelating groups. The carboxylic groups, ester groups, amino groups, or amide groups bind to $D_n$, and the chelating groups bind to the metal cations.

4 Claims, No Drawings

DENDRITIC COMPOUND AND USE THEREOF

BACKGROUND OF THE INVENTION

1. Field of the Invention

The present invention relates to a dendritic compound, and more particularly, to a dendritic compound suitable for chelating with metal cations.

2. Description of Related Art

Nuclear Magnetic Resonance Imaging (MRI) is one of the most significant diagnosing techniques in modern medical science. Compared to X-rays or CT scanning, MRI provides multi-angle scanning which can be applied to the central nerve system, the skeletal nerve system, the abdomen, the chest, angiography, cholangiography, and the most important and valuable of all, to discover and diagnose tumor tissues.

The principle of MRI is to transform the hydrogen atoms within human tissues into tiny radio transmitters. Under the same magnetic field change, hydrogen atoms within water or other molecules transmit different signals. MRI traces these signals and forms the 3-D image of a human body through Fourier Transfer. In other words, the greater the differences in each radio-transmitted signal, the clearer contrast will be transformed. So far, it is known that the use of super-paramagnetic elements, such as Gadolinium (Gd), can enhance the contrast. As a result, the density of super-paramagnetic elements is the critical factor for the clarity of image.

In addition, due to the fact that free Gd is toxic, a chelator must be added when the Gd is applied to human bodies. The addition of the chelator can decrease the chemical reaction during body circulation. Diethylenetriamine pentaacetic acid (DTPA) is one of the most common and commercially mass produced chelators for application in MRI.

However, when applying the commercialized non-polymer carrier Gd-DTPA as an imaging agent, chelators with small molecule weight penetrate vascular endothelial cells easily and thus extensive losses occur while circulating. Furthermore, it requires high concentration of Gd to achieve the desirable image. In addition to the potential danger of toxicity caused by high concentration of Gd, it is also difficult to massively accumulate an imaging agent on a certain position. Therefore, there exists a great disadvantage for clinical application of prior art non-polymer Gd-DTPA imaging agents.

SUMMARY OF THE INVENTION

The present invention provides a dendritic compound of the following structure (I):

$$PD_n\text{-}Z\text{-}L \quad (I)$$

wherein,
P is X—$(CH_2CH_2$—$O)_r$—, r is an integer equal to 1 or greater than 1, X is OH, $NH_2$ or OR, and R is $C_1$ to $C_{10}$ alkyl;

$D_n$ is a residue of branched $C_3$ to $C_{30}$ polyol compounds, n is the quantity of layers of the residue of branched compounds and n is an integer equal to or greater than 1;

L is metal cations; and

Z is the residue of a $C_3$ to $C_{30}$ compounds with multi functional groups;

wherein, the functional groups are carboxylic groups, amino groups, ester groups, amide groups, or chelating groups; and the carboxylic groups, ester groups, amino groups, or amide groups bound to Dn, and the chelating groups bound to the metal cations.

The dendritic compound of the present invention can be any conventional poly ethylene glycol derivative, but preferably is poly ethylene glycol. $D_n$ in the dendritic compound of the present invention can be any residue of $C_3$ to $C_{30}$ branched polyol compounds, but preferably is 2,2-bis(hydroxymethyl) propionic acid or the residue of its derivatives, DTPA residue, residue of DTPA derivatives, or the combination thereof.

Furthermore, the quantity of layers (n) of the dendritic compound of the present invention is not limited, but preferably n=3. L in the dendritic compound of the present invention can be any metal ion with biological toxicity, but preferably is Gd. Finally, Z can be any residue of $C_3$-$C_{20}$ compounds with multiple functional groups, but preferably is residue of ethylenedinitrilo tetraacetic acid (EDTA), or that of ethylenediimino dibyric acid (EDBA). The more preferable is the residue of the compound having the structure of formula (IV) below.

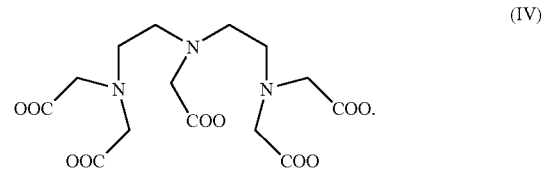

(IV)

DETAILED DESCRIPTION OF THE PREFERRED EMBODIMENT

In this invention, linear polyethylene glycol and 2,2-bis (hydroxymethyl)propionic anhydride are used as starting materials. Diethylenetriaminepentacetic acid (DTPA) is the chelator to stabilize Gd.

EXAMPLE 1

Preparation of dendritic compound P-$D_1$-(DTPA)

a. Preparation of the First Generation Benzylidene Protected Chelate P-$D_1$-($O_2$Bn)

PEG diol (MW 4000 Da, 9.2 g, 2.3 mmol, 1 eq) and DMAP (0.1670 g, 0.39 mmol) are mixed in a round-bottom conical vial. The mixture is dissolved in a 25 mL of DCM and then the vial is filled with nitrogen gas. Benzylidene-2,2-bis(oxymethyl)propionic anhydride (4.27 g (10 mmol)) is dissolved in another vial, and then slowly dripped into the reaction vial. After 24 hours of stirring and reacting in room temperature, 10 ml methanol is added and the reaction is kept for another 6 hours for removing the un-reacted Benzylidene-2,2-bis (oxymethyl)propionic anhydride. An excessive amount of ethyl ether (700 mL) is added and the mixture is stirred until white precipitates are released, and the yield rate is about 90%. Among the products, the $D_n$ is $D_1$ with the structure of (I) as follows:

(I)

IR (cm-I): 2890, 1738, 1150.
$^1$H NMR (400 MHz, CDCl$_3$): δ 1.06 (s, 6), 3.55 (t, 6), 3.61 (bs), 3.68 (t, 6), 4.32 (t, 4), 4.64 (d, 4), 5.43 (s, 2), 7.28 (m, 6), 7.42 (m, 4).

b. Preparation of Chelate P-D$_1$-(OH)

After the above product (11.8 g) is dissolved in 40 mL of 1:2 CH$_2$Cl$_2$/MeOH solution, 1.18 g of Pd/C is added, and the mixture is stirred for 24 hours under a hydrogen-saturated environment. When the reaction ends, Pd/C is filtrated from DCM, and as described above, an excessive amount of ethyl ether 600 (mL) is added to release the white precipitates. The yield rate of the product after freeze-drying is approximately 90%.

IR (cm-I): 3480, 2890, 1725, 1148.
$^1$H NMR (400 MHz, CDCl$_3$): δ 1.08 (s, 6), 3.67 (bs), 4.31 (t, 4).

c. Synthesis of P-D$_1$-DTPA

P-D$_1$-OH ( 2.0 g, 0.4618 mmol) and diethylenetriaminepentaacetic acid mono-N-hydroxysuccinimide ester (DTPA-HSIE) (1.0871 g, 2.2 mmol) are mixed in a 50 mL round-bottom conical vial and vacuum dried for 3 hours. Anhydrous DMSO (10 mL) and Triethylamine (224 µL) are injected into the mixture and stirred for 48 hours at room temperature under saturated nitrogen gas. Acetonitrile/acetone is used to release white residue; the white solid product after centrifugation and freeze-drying is P-D$_1$-DTPA.

IR (cm-1): 3446, 2888, 1714, 1638, 1109.
$^1$H NMR (400 MHz, CDCl$_3$): δ 1.14 (s, 6), 3.1 (t, 16), 3.4 (t, 16), 3.57 (bs), 3.75 (s, 8), 3.8 (s, 32).

EXAMPLE 2

Preparation of Dendritic Compound P-D$_2$-(ODTPA)

a. Preparation of Chelate P-D$_2$-(O$_2$Bn)

The principle of preparing the second generation P-D$_2$-(O$_2$Bn) product is approximately the same as that of the first generation. P-D$_1$-(O$_2$Bn) (95.6 g, 0.83 mmol, 1 equiv) and DMAP (0.326 g, 2.6 mmol, 3.2 equiv) is mixed and then dissolved in 25 mL DCM. After Benzylidene-2,2-bis(oxymethyl)propionic anhydride (13.3 mmol, 16 equiv, 5.69 g) is added, the mixture is stirred at room temperature for 24 hours. Un-reacted Benzylidene-2,2-bis(oxymethyl)propionic anhydride is removed with 15 mL Methanol. Then ethyl ether is used to release the white precipitate at a yield rate of 80% after freeze-drying. The product D$_n$ is D$_2$ with the structure (II) as follows:

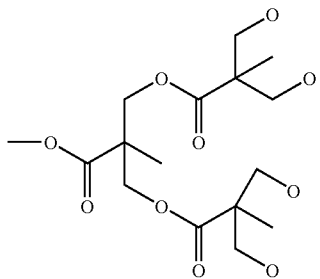

(II)

IR (cm-I): 2885, 1740, 1100.
$^1$H NMR (400 MHz, CDCl$_3$): δ 1.03 (s, 12), 1.26 (s, 6), 3.63 (bs), 3.78 (t, 4), 4.03 (t, 4), 4.38 (s, 8), 4.56 (d, 8), 5.41 (s, 4), 7.19 (m, 12), 7.38 (m, 8).

b. Preparation of chelate P-D$_2$-OH

The product (5.5 g) from the above process is dissolved in 45 mL of 1:2 DCM/MeOH solution. The de-protection procedure in step b. of example 1 is repeated, and the final yield rate is about 88%.

IR (cm-1): 3401, 2887, 1727, 1108.
$^1$H NMR (400 MHz, CDCl$_3$): δ 1.03 (s, 12),1.19 (s,6), 3.43 (m, 8), 3.64 (bs), 4.08 (m, 8), 4.40 (d, 4).

c. Synthesis of P-D$_2$-DTPA

The method of synthesizing the second generation P-D$_2$-DTPA is approximately the same as that of first generation. P-D$_2$-OH (0.265 mmol, 1.3965 g) and 1.2482 g (2.54 mmol) DTPA-HSIE is mixed in a 50 mL round bottom conical vial and vacuum dried for 4 hours. Anhydrous DMSO (10 mL) and 350 µL Triethylamine is injected into the mixture, and stirred for 48 hours at room temperature under saturated nitrogen gas. Acetonitrile/acetone solution is used to release the white precipitate, and P-D$_2$-DTPA is produced after centrifugation and freeze-drying.

IR (cm$^{-1}$): 3438, 2939, 2678, 1725, 1634, 1228.
$^1$H NMR (400 MHz, CDCl$_3$): δ 1.04 (m), 1.18 (m), 3.07 (t, 16), 3.21 (t, 16), 3.58 (bs), 3.68 (m), 3.79 (d), 4.21 (bs).

EXAMPLE 3

Preparation of Dendritic Compound P-D$_3$-(DTPA)

a. Preparation of chelate P-D$_3$-(O$_2$Bn)

The preparation process of the third generation P-D$_3$-(O$_2$Bn) is similar to that of the first and second generations. The product from step b. in example 2 (2.88 g, 0.40 mmol, 1 equiv), Benzylidene-2,2-bis(oxymethyl)propionic anhydride (5.48 g, 12.8 mmol, 32 equiv), and DMAP (0.3151 g, 2.57 mmol, 6.4 equiv) are dissolved in 35 mL DCM at room temperature and reacted for 24 hours. The extracting procedure in step a. of example 2 is repeated, and the final product yield rate is about 89%. The D$_n$ product is D$_3$ with the structure of (III) as follows.

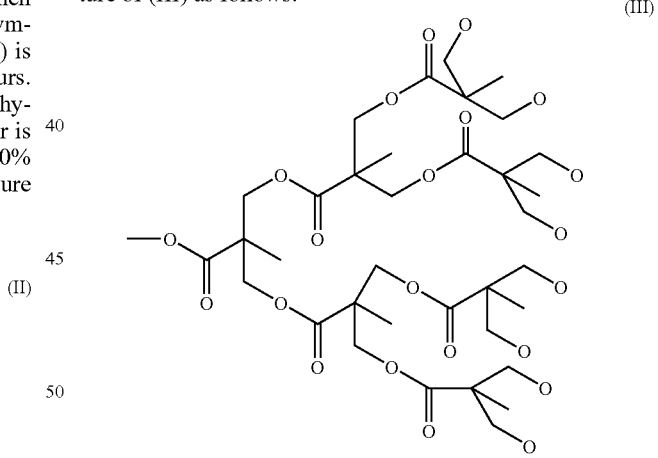

(III)

$^1$H NMR (400 MHz, CDCl$_3$): δ 0.89 (s, 24), 1.16 (s, 6), 1.17 (s, 12), 3.57 (t, 6), 3.67 (bs), 3.77 (t, 3), 4.15 (q, 6), 4.28 (t, 3), 4.33 (m, 16), 4.55 (d, 16), 5.37 (s, 8), 7.30 (m, 24), 7.35 (m, 16).

b. Preparation of Chelate P-D$_2$-OH

The product (4 g) from step a. is dissolved in the mixture of DCM and MeOH (1: 1). Pd/C catalyst (0.4 g) is added, and stirred for 24 hours under a hydrogen-saturated environment. White powder product (1.8 g) is produced after filtering and freeze-drying.

$^1$H NMR (400 MHz, CDCl$_3$): δ 1.07 (s, 24), 1.27 (s, 6), 1.34 (s, 12), 3.47 (t), 3.64 (bs), 3.76 (m), 4.26 (m), 4.32 (dd, 10).

c. Synthesis of P-D$_3$-DTPA.

The method of synthesizing the third generation P-D$_3$-DTPA is the same as aforementioned. P-D$_3$-OH (1.097 g, 0.1938 mmol) and 1.814 g (3.6 mmol) DTPA-HSIE are mixed in a 50 mL round bottom conical vial and vacuum dried for 4 hours. Anhydrous DMSO (10 mL) and 515 µL Triethylamine are injected into the mixture, and stirred for 64 hours at room temperature under saturated nitrogen gas. After white precipitate is released by means of acetonitrile/acetone solution, the white solid product, P-D$_3$-DTPA, is produced after centrifugation and freeze-drying.

IR(cm$^{-1}$): 3460, 2990, 2650, 1720, 1645, 1235.

$^1$H NMR (400 MHz, CDCl$_3$): δ 1.03 (s), 1.25 (s), 1.29 (s), 2.7 (m), 3.16 (t), 3.46 (t), 3.79 (bs), 3.80 (m), 3.97 (bs), 4.21 (m).

In the P-D$_n$-DTPA dendritic compounds of the first, second and third generation, the resonant frequency in NMR spectrum of the methyl on hydrogen is decreased as the generation extends. Therefore, it is proved that the dendritic compound of P-D$_n$-DTPA in the present example is the dendritic compound of the first, second and third generations. In addition, infrared spectrum can be applied to verify the structure of DTPA; in other words, the original C—O bond of DTPA is disappeared at the peak of 1200 cm$^{-1}$, and instead, the carbonyl peak is appeared between signals of 1638 and 1598 cm$^{-1}$. As a result, it is proved that the dendritic compound in the present example possesses the DTPA to chelate Gd.

EXAMPLE 4

Preparation of the Final Complex P-D$_3$-DTPA-Gd$^{3+}$

P-D$_3$-DTPA (0.066 g, 0.005 mmol) is dissolved in 10 mL water, and a 16-time amount of GdCl$_3$.6H$_2$O (0.031 g, 0.08 mmol) is added. The pH value is adjusted in neutral (pH7) by 0.1 N sodium hydroxide solution. The result of the reaction is verified by FTIR and white solid product is produced after freeze-drying.

IR (cm$^{-1}$): 3426, 2919, 1615.

Characteristic Testing

By evaluating the effectiveness of the reacted dendritic compound P-D$_3$-DTPA-Gd$^{3+}$ of the third generation as an agent of enhancing image, it can be compared with the magnetizing relaxation of DTPA-Gd (Magnevist™) by directly comparing the magnetizing relaxation rate via NMR. The results of comparison are showed in Table 1 in which R$_1$ and R$_2$ respectively represent vertical and horizontal relative relaxation times, and B$_0$ as the internal magnetic intensity of NMR. The greater volumes of R$_1$ and R$_2$, the stronger image signal will be. Therefore, Table 1 is clearly indicated the chelating Gd element of third generation dendritic compound provides a superior imaging result compared to DTPA-Gd (Magnevist™), and demonstrated distinct progress in NMR imaging.

TABLE 1

| Compound | R$_1$(20 MHz) B$_0$ = 0.47T | R$_2$ B$_0$ = 0.47T | Literature |
|---|---|---|---|
| Magnevist ™ | 6.14 | 5.84 | R$_1$ = 3.4 R$_2$ = 3.8 B$_0$ = 1.0T |
| PEG-G3-DTPA-Gd$^{3+}$ | 305 | 312.5 | NIL |

Furthermore, conventional imaging agents require high concentration of Gd to achieve the ideal image, and it is also a challenge to accumulate the imaging agent on a certain location. The dendritic compound in this invention provides a vivid and clear image with no need to accumulate the image agent on one position and this situation promotes a more suitable clinical application.

In addition, each dendritic compound in the present invention contains protected OH functional groups, which extend to a higher generation and possesses the magnifying ability by times. Therefore, compared to known imaging agents, a better imaging contrast is provided with the same amount. It is also known that chelator with small molecule weight penetrates vascular endothelial cells easily such that it disperses while circulating; the dendritic compound is a high molecule carrier which decreases the possibility of being drained away during blood circulation.

The "core" of the dendritic compound of the present invention is polyethylene glycol and its derivatives. Polyethylene glycol, a bio-compatible polymer certified by the FDA in the USA, is usually applied to biomedical polymers and can be eliminated spontaneously via circulation. Therefore, the dendritic compound of the present invention can be an imaging agent with low toxicity.

What is claimed is:

1. A dendritic compound of structure (I):

PD$_n$-Z-L                 (I)

wherein

P is X—(CH$_2$CH$_2$—O)$_r$—, r is an integer equal to 1 or greater than 1, X is OH, NH$_2$ or OR, and R is C$_1$ to C$_{10}$ alkyl;

Dn is a residue selected from the group consisting of 2,2-bis(hydroxymethyl)propionic acid, D$_1$ having a structure of formula (I):

(I)

D$_2$ having a structure of formula (II):

(II)

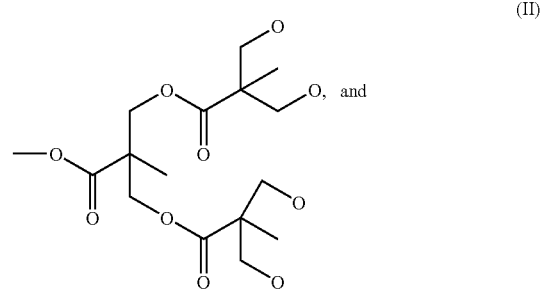

D₃ having a structure of formula (III):

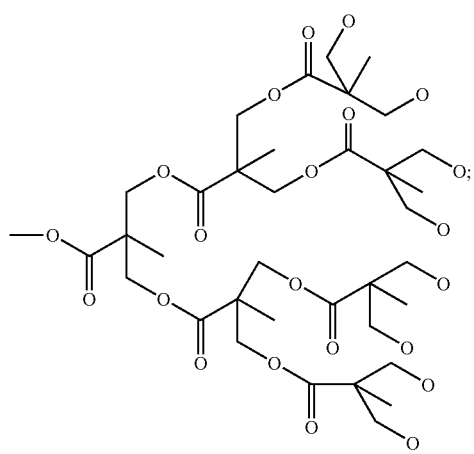

(III)

L is a metal cation; and

Z is a residue of ethylenedinitrilo tetraacetic acid (EDTA), ethylenedilmino dibyric acid (EDBA), or a compound having a structure of formula (IV):

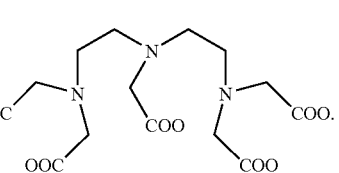

(IV)

2. The dendritic compound as claimed in claim 1, wherein P is polyethylene glycol.

3. The dendritic compound as claimed in claim 1, wherein L is Gadolinium (Gd).

4. The dendritic compound as claimed in claim 1, wherein L is Gadolinium (Gd), and P is polyethylene glycol.

* * * * *